United States Patent [19]
Nedwig

[11] 3,990,149
[45] Nov. 9, 1976

[54] ADHESIVE FOIL FOR DENTAL PROSTHESIS AND A METHOD OF MANUFACTURING IT

[76] Inventor: Otto Nedwig, 8752 Sternberg, Germany

[22] Filed: Mar. 20, 1975

[21] Appl. No.: 560,192

[30] Foreign Application Priority Data
Mar. 20, 1974 Germany............................ 2413380

[52] U.S. Cl. .................................. 32/2; 32/DIG. 2
[51] Int. Cl.² ........................................ A61C 13/00
[58] Field of Search ..................... 32/2, DIG. 2, 3, 1

[56] References Cited
UNITED STATES PATENTS

| | | | |
|---|---|---|---|
| 1,050,561 | 1/1913 | Moore | 32/DIG. 2 |
| 2,392,513 | 1/1946 | Town | 32/DIG. 2 |
| 2,929,143 | 3/1960 | Roubeau | 32/1 |
| 3,226,826 | 1/1966 | Town | 32/2 |

FOREIGN PATENTS OR APPLICATIONS

| | | | |
|---|---|---|---|
| 1,566,252 | 11/1970 | Germany | 32/2 |
| 460,887 | 1/1937 | United Kingdom | 32/2 |

*Primary Examiner*—Jack Q. Lever

[57] ABSTRACT

An adhesive foil for dental prostheses comprising a compressed fiber mat containing a dry adhesive which swells under the action of the moisture in the mouth, the fibers being interconnected by an adhesive which is not dissolved by the moisture in the mouth, characterized in that the concentration of adhesive is greater in the central cross-sectional region of the mat than in the regions near the surface, and the method of preparing same.

8 Claims, 1 Drawing Figure

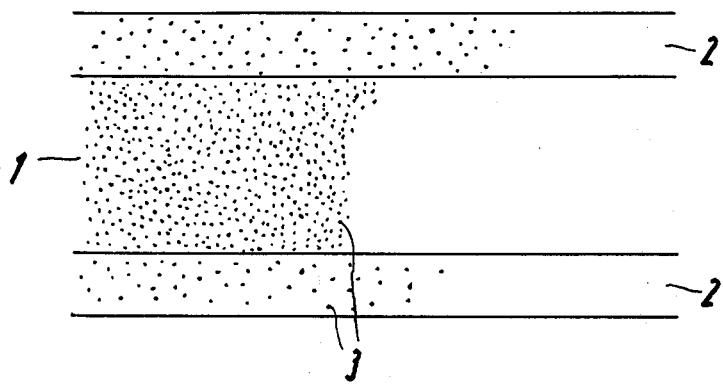

ADHESIVE FOIL FOR DENTAL PROSTHESIS AND A METHOD OF MANUFACTURING IT

The invention relates to an adhesive foil for dental prosthesis comprising a compressed fibre mat containing a dry adhesive which swells under the action of the moisture in the mouth, the fibres being interconnected by an adhesive which is not dissolved by the moisture in the mouth.

Various kinds of adhesive foil for dental prosthesis have already been developed. They comprise a flexible supporting foil and an adhesive. This type of foil has not given good results in practice, since the adhesive is washed away by the mouth fluid and the carrier foil is insufficiently adaptable and tends to form folds at the curved portions of the palate and jaws.

In practice, therefore, it is more normal to use adhesives which are inserted between the prosthesis and the palate or jaw in the form of a paste or a powder which swells in the mouth fluid, without using a support. The adhesives form a gel which compensates differences in the gaps between the prosthesis and the palate or jaw. The adhesive effect is due to the fact that irregularities in the gaps are evened out, rather than to the adhesive action. Since, however, these substances are dissolved or diluted in the mouth fluid, they are gradually washed out and therefore retain the desired consistency at the desired place for only a limited time.

Finally, German Pat. Specification No. 1,566,252 discloses an adhesive foil comprising a compressed fibre mat containing a dry adhesive which swells under the effect of the mouth fluid, the fibres being secured together by an adhesive which does not dissolve in the mouth fluid. The adhesive foil, like those previously mentioned, is inserted between the prosthesis and the palate or jaw. The adhesive swells in the mouth fluid and forms a gel, as is known in the case of adhesive powders or pastes, which compensates differences in the gap between the prosthesis and the palate or jaw. The mat can, without folding, adapt to the shape of the prosthesis, and also adapts to the adhesive when it swells, so that the fibres extend in a uniform, statistical manner through the adhesive gel member formed between the prosthesis and the palate or jaws and strengthen it, like the concrete skeleton of a reinforced concrete structure. Individual fibres cannot come loose and penetrate into the mouth, since they are stuck or joined together, e.g. by additional adhesives or by thermoplastic welding of the fibres.

An important feature of the aforementioned adhesive foil is that the fibres, in the state in which they are used, are relatively uniformly distributed in a gel member. This object has previously been achieved by distributing the dry powdered adhesive in a very uniform manner over the entire cross-section of the mat. The disadvantage of this method, however, is that the tools used for pressing the mat after the adhesive has been applied, easily come in contact with the adhesive and are consequently soiled. When the powdered adhesive is dispersed in the mat, which is still loose before pressing, the resulting concentration of adhesive may easily be higher on one side than on the other, with the disadvantageous result that the fibres are not distributed in the aforementioned optimum uniform manner in the gel member.

The invention relates to a known adhesive foil for dental prosthesis comprising a compressed fiber mat containing a dry adhesive which swells under the action of mouth fluid and wherein the fibres are secured together by an adhesive which is not dissolved by the mouth fluid. An object of the invention is to improve the last-mentioned foil, so that soiling of the pressing tools is avoided and the adhesive effect is very uniform on both sides of the foil.

To this end, according to the invention, the concentration of adhesive greater in the central cross-sectional region of the mat than in the regions near the surface. This solution appears to go against the requirement of obtaining a uniform distribution of fibres in the gel member. Experience shows, however, that a higher concentration of fibres in the region near the surface has an advantageous effect in strengthening the gel member and in securing it at the required place. The adhesive effect occurs at about the same speed on both sides. Another advantage is that the pressing tools do not come in direct contact with the adhesive and therefore do not have to be cleaned so often.

Preferably, the adhesive is disposed so that at least 75% of it is present in the central region, i.e. in the central three-fifths of the foil cross-section. In a preferred embodiment, the regions of the foil near the surfaces do not contain any appreciable amount of adhesive.

In a particularly advantageous embodiment, the adhesive foil according to the invention comprises a main layer containing most of the adhesive and at least one cover layer which is substantially free of adhesive. If the foil is constructed in this manner, the surface parts thereof can be made from separate cover mats which are not impregnated with adhesive during manufacture. Consequently, when the adhesive foil is ready for use, the surface regions will contain only a small quantity of adhesive which has been driven into them during the mat-pressing operation. Of course, both sides of the foil can be provided with a cover layer of this kind. But it is often sufficient to provide a cover layer on only one surface on the main layer, i.e. on the side from which the adhesive is dispersed into the main layer. Another advantage of using a cover layer is that the material used at the surface of the foil can be softer than the material used for retaining the adhesive in the central region. The resulting adhesive foil retains the adhesive in optimum manner and also has pleasant surface properties.

Another advantage of disposing the adhesive mainly in the central region of the foil is that the foil is relatively insensitive. The adhesive cannot be squeezed out so easily by mechanical stress, and the foil does not become sticky so quickly if its surface are accidentally exposed to moisture.

In an advantageous method of manufacturing the foil according to the invention, the adhesive is dispersed in known manner in the freshly-cut mat while it is still very loose, after which a cover mat is placed on the side where the adhesive was inserted. The other side also can be provided with a cover layer. Next, all the layers are compressed together, advantageously with heating and in the presence of moisture. The heating is designed to produce thermoplastic softening of at least some of the fibres forming the mat, which thus stick together. At least some of the fibres, therefore, should be made of thermoplastic material. The moisture softens the particles of adhesive, which are therefore more uniformly distributed in the foil. However, the softening of the adhesive and the pressure should not be great enough for the adhesive to penetrate the surface regions of the foil.

In an advantageous embodiment in which only one cover layer is required, the adhesive is dispersed in the main layer so that it penetrates only a top part thereof, whereas a bottom part of the main layer remains substantially free from adhesive. In this case, only the upper side of the main layer needs to be provided with a cover mat, since the bottom part of the main layer is in any case substantially free from adhesive.

The fibre content of the adhesive foil, i.e. the part which remains after the adhesive has been washed out of the foil, advantageously has a weight of 80 – 120 grams per square meter. Preferably the weight of the main layer is 50 – 80 grams per square meter and the weight of the cover layer or layers is 20 – 35 grams.

When the cover layer is placed on the main layer, it need not be in the same loose state as the main layer, but can be wholly or partly solidified by pressure. If there is a difference between the roughness of the two sides of the cover layer, the rougher side should preferably face the main layer, thus providing a more intimate connection.

Instead of applying heat during pressing, other means such as suitable adhesives can be used for securing the fibres together. These need not be described in detail here, however, since features of this kind are known in the art and the invention is not concerned with methods of joining fibres.

The single drawing is a large-scale diagrammatic cross-section through a finished adhesive foil, showing a main layer 1 and a cover layer 2. The concentration of adhesive is indicated by dots 3, the spacing between which varies.

I claim:

1. An adhesive foil for dental prosthesis comprising a compressed fibre mat containing a dry adhesive, swells under the action of the moisture in the mouth, the fibres being interconnected by an adhesive, which is not dissolved by the moisture in the mouth, and the concentration of adhesive being greater in the central cross-sectional region of the mat than in the regions near the surface.

2. An adhesive foil according to claim 1, wherein at least 75% of the adhesive is in the central three-fifths of the thickness of the mat.

3. An adhesive foil, according to claim 2, wherein said mat comprises a main layer containing most of the adhesive and at least one cover layer which is substantially free from adhesive.

4. An adhesive foil according to claim 3, wherein the cover layer is softer than the main layer.

5. An adhesive foil according to claim 3 wherein the cover layer has a weight of 20 – 35 grams per square meter and the main layer has a weight of 50 – 80 grams per square meter.

6. A method for preparing an adhesive foil for dental prosthesis, which comprises impregnating a loosely formed fibre mat with an adhesive, which swells under the action of the moisture in the mouth, said adhesive being disposed so that, at least, 75% is present in a central region of said mat and greater in a central cross-sectional region than in regions near the surface of said mat, placing at least one cover layer on said mat, and then compressing the formed structure, so as to secure the said at least one cover layer to said mat.

7. A method, according to claim 6, wherein the adhesive is so dispersed in dispersible form in the main layer, when the latter is in a loose form, that it penetrates only a top part of the layer, whereas a bottom part of the layer remains substantially free from adhesive, and only one cover layer is used, the cover layer being disposed on that surface of the main layer, which is upper most when the adhesive is dispersed therein.

8. A method, according to claim 6, wherein said cover layer has a weight of 20–35 grams per square meter and the mat has a weight of 50–80 grams per square meter.

* * * * *